(12) United States Patent
Dañino

(10) Patent No.: US 11,559,452 B1
(45) Date of Patent: Jan. 24, 2023

(54) POWERED MANAGED THERAPEUTIC SUPPORT SURFACE SYSTEM FOR THE TREATMENT OF PRESSURE INJURIES

(71) Applicant: Rafael Dañino, Lima (PE)

(72) Inventor: Rafael Dañino, Lima (PE)

(73) Assignee: Rafael Daniño-Incháustegui, Lima (PE)

( * ) Notice: Subject to any disclaimer, the term of this patent is extended or adjusted under 35 U.S.C. 154(b) by 0 days.

(21) Appl. No.: 17/669,846

(22) Filed: Feb. 11, 2022

Related U.S. Application Data

(60) Provisional application No. 63/283,974, filed on Nov. 29, 2021.

(51) Int. Cl.
*A61G 7/018* (2006.01)
*A61G 7/043* (2006.01)
(Continued)

(52) U.S. Cl.
CPC .......... *A61G 7/05776* (2013.01); *A61F 7/007* (2013.01); *A61H 9/0007* (2013.01); *A61M 21/02* (2013.01); *A61F 2007/0086* (2013.01); *A61F 2007/0093* (2013.01); *A61F 2007/0096* (2013.01); *A61G 2203/20* (2013.01); *A61G 2203/30* (2013.01); *A61G 2203/46* (2013.01); *A61H 2201/1207* (2013.01); *A61H 2201/5005* (2013.01); *A61H 2201/5007* (2013.01); *A61H 2201/5046* (2013.01);
(Continued)

(58) Field of Classification Search
CPC .......... A47C 27/10; A47C 27/085; A47C 4/54
See application file for complete search history.

(56) References Cited

U.S. PATENT DOCUMENTS

| 3,872,526 A | 3/1975 | Betts |
|---|---|---|
| 3,999,235 A | 12/1976 | Mollura |

(Continued)

FOREIGN PATENT DOCUMENTS

| CN | 204273890 | 4/2015 |
|---|---|---|
| CN | 108514281 | 9/2018 |

(Continued)

OTHER PUBLICATIONS

IZone Bed; izone Hybrid Waterbed Mattresses; Date: Feb. 8, 2021; By: Boyd Flotation.
(Continued)

*Primary Examiner* — Christine H Matthews
*Assistant Examiner* — Joshua Daryl D Lannu
(74) *Attorney, Agent, or Firm* — Caldwell Intellectual Property Law

(57) ABSTRACT

A pressure injuries therapeutic support surface is illustrated. The surface comprises an integrated system designed for a concurrent physical and psychoneuroimmunological approach over a user, wherein the system comprises one or a plurality of independent fluid-filled main chambers, made of waterproof, flexible, extendable, and elastic material and at least two accessory chambers connected to each main chamber with at least with two free-flow conduits. The system is managed through a powered mechatronic array with its own hardware and software based on microcontrollers for the simultaneous operation of specific multidisciplinary devices.

24 Claims, 13 Drawing Sheets

(51) Int. Cl.
  *A61H 9/00* (2006.01)
  *A47C 21/00* (2006.01)
  *A61G 7/057* (2006.01)
  *A61F 7/00* (2006.01)
  *A61M 21/02* (2006.01)
  *A61M 21/00* (2006.01)

(52) U.S. Cl.
  CPC ............... *A61H 2201/5058* (2013.01); *A61H 2201/5082* (2013.01); *A61M 2021/0027* (2013.01); *A61M 2021/0066* (2013.01); *A61M 2205/3317* (2013.01); *A61M 2205/3368* (2013.01); *A61M 2205/505* (2013.01)

(56) References Cited

U.S. PATENT DOCUMENTS

| | | |
|---|---|---|
| 4,297,755 A | 11/1981 | Mollura |
| 4,558,476 A | 12/1985 | Linder |
| 4,652,726 A | 3/1987 | Femino |
| 4,907,307 A | 3/1990 | Weitzler |
| 5,020,176 A | 6/1991 | Dotson |
| 5,062,169 A | 11/1991 | Kennedy et al. |
| 5,850,644 A | 12/1998 | Hsia |
| 9,265,352 B2 | 2/2016 | Oakhill |
| 2003/0019041 A1* | 1/2003 | Inchaustegui ........... A47C 27/10 5/665 |
| 2004/0239171 A1* | 12/2004 | Inchaustegui ............ A47C 4/54 297/452.41 |
| 2010/0301640 A1* | 12/2010 | Heiser ..................... A47C 1/11 297/135 |

FOREIGN PATENT DOCUMENTS

| | | |
|---|---|---|
| DE | 9409944 | 9/1994 |
| DE | 10024299 | 11/2001 |
| DE | 20315896 U1 | 1/2004 |
| DE | 202008007322 | 7/2008 |
| DE | 102007027278 | 12/2008 |
| DE | 102011075524 | 10/2016 |
| EP | 0226699 | 7/1987 |
| EP | 1415575 | 5/2004 |

OTHER PUBLICATIONS

Starpool Wave Bed; Commercial relaxation water bed WAVE; By: STARPOOL; Date: Feb. 8, 2021.

\* cited by examiner

POWERED MANAGED THERAPEUTIC SUPPORT SURFACE SYSTEM FOR THE TREATMENT OF PRESSURE INJURIES

CROSS-REFERENCE TO RELATED APPLICATIONS

This application claims the benefit of priority of U.S. Provisional Patent Application Ser. No. 63/283,974, filed on Nov. 29, 2021, and titled "POWERED PRESSURE INJURIES SUPPORT SURFACE," which is incorporated by reference herein in its entirety.

FIELD OF THE INVENTION

The present invention generally relates to the field of therapeutic support systems. In particular, the present invention is directed to a powered managed therapeutic support surface system for the treatment of pressure injuries.

BACKGROUND

The most widely used mattresses today are diverse types of foam mattresses, air mattresses employing alternating compressed air chambers, and/or gel mattress overlays. All of these, when used, exhibit an almost-solid final behavior when they compress or compact upon receiving a load such as a human body. Such almost-solid behavior of sleep surfaces contributes to widespread and costly pressure injuries in treatment facilities around the world. Pressure injuries are an area of unrelieved pressure usually over a bony prominence leading to ischemia, cell death, and tissue necrosis. Pressure injuries have been defined as "an area of unrelieved pressure usually over a bony prominence leading to ischemia, cell death, and tissue necrosis." Pressure ulcers are the third most expensive disorder after cancer and cardiovascular diseases. Pressure injuries are known to be the costliest and most physically debilitating complication of the 20th century; it affects 2.5 million people in the United States, has a $12 billion industry trying to treat it, causes 60,000 deaths, and 17,000 legal actions per year. Two-thirds of pressure sores occur in the elderly above 70 years of age, although it is also common in young users with neurological impairment. Pressure injuries have a 68.8% mortality amongst elderly users with National Pressure Injury Advisory Panel ("NPIAP") stage III and IV pressure ulcers, because of secondary systemic complications. Overall, pressure ulcers hamper the quality of life, and the prevention of pressure ulcers is an important goal. SUMMARY OF THE DISCLOSURE In an aspect, a powered managed therapeutic support surface system for the treatment of pressure injuries is illustrated. The surface comprises an integrated system designed for a concurrent physical and psychoneuroimmunological approach over a user, where the system comprises at least one independent fluid-filled main chambers, made of waterproof, flexible, extendable, and elastic material and at least two corresponding accessory chambers connected to the at least one independent chamber fluidically connected to at least two free-flow conduits. The system is managed through a powered mechatronic array controlled by hardware and software based on microcontrollers for the simultaneous operation of multidisciplinary devices.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
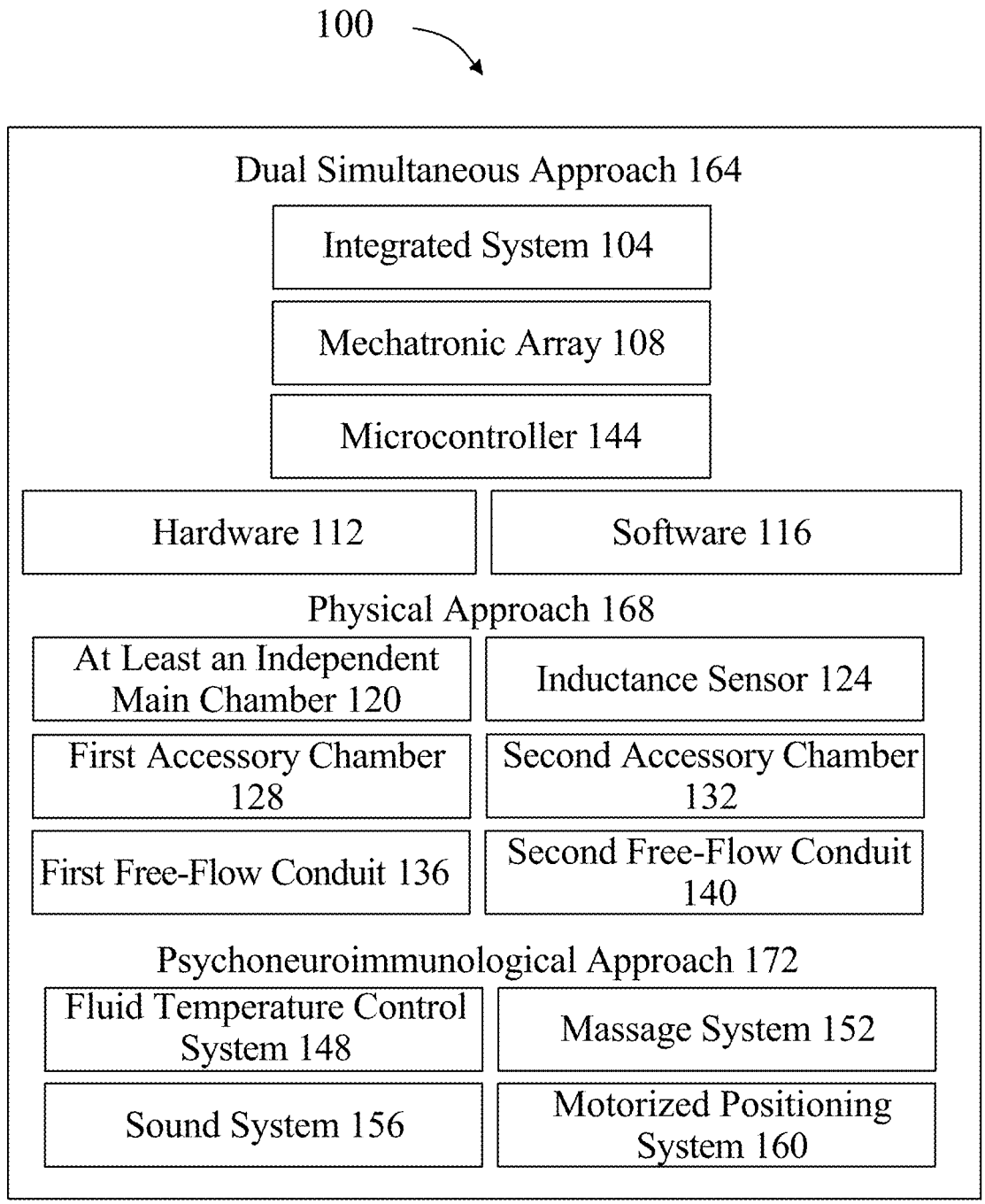
FIG. 1 illustrates a block diagram for a powered managed therapeutic support surface system for the treatment of pressure injuries.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure include a powered managed therapeutic pressure injuries support surface. Aspects of the present disclosure include an integrated system designed for a concurrent physical and psychoneuroimmunological approach over a user. Aspects of the present disclosure include the system comprising one or a plurality of independent fluid-filled main chambers, made of waterproof, flexible, extendable, and elastic material. Aspects of the present disclosure include the system comprising at least two corresponding accessory chambers connected to each main chamber with at least two free-flow conduits. Aspects of the present disclosure include the system being managed through a powered mechatronic array with its own hardware and software based on microcontrollers for the simultaneous operation of specific multidisciplinary devices.

The present invention discloses a support surface designed to actuate, simultaneously, both the body and mind of a user for an integrated physical and psychoneuroimmunological approach to the treatment of pressure injuries. This disclosure improves on pressure reduction by increasing the contact area through immersion and envelopment described as the depth of penetration or sinking and the ability of a support surface to conform, so to fit or mold around irregularities in the body, respectively. Surrounding the body by a fluid that provides a newly support, diminishing pressure and providing a better distribution. The physical characteristics of the main chambers are managed by the flow of a fluid to a first accessory chamber, which changes its volume size or vertical position. An empty second accessory chamber dissipates any pressure, to assist the main chamber in eliminating pressure points and preventing pressure injuries. Temperature, massage, music, and positioning devices are included to induce a relaxed mental state in the user, which uses psychoneuroimmunology to generate crucial benefits for the user. Designed primarily for the prevention and/or treatment of pressure injuries, the support surface can also help other diseases treatments.

The system also takes a psychoneuroimmunological approach to the treatment of pressure injuries. Psychoneuroimmunological therapeutic benefits further interact along with the said managed physical characteristics of the main chambers. Psychoneuroimmunology (PNI) is the study of the relationship between the immune system, the endocrine system, and the central and peripheral nervous system. It is newly studied within the past forty years and has intensely evolved over the last ten years. PNI is essentially an integrative discipline, meaning it relates mental processes to the function of the immune system and how, in turn, immunological activity is capable of altering the function of the mind. Research pointing to a circuit linking the immune system and brain connects illness, stress, mood and thought in a whole new way. Research also shows that the immune system sends signals to the brain to alter neural activity, thus altering behavior, thought and mood of the person since these are controlled by neural activity. The brain communicates with the immune system through autonomic nervous system and neuroendocrine activity. Both autonomic nervous system activity and neuroendocrine activity generate signals that are perceived by the immune system via receptors on the surface of immune cells. Moreover, neurotransmitters, hormones, and neuropeptides have been found to regulate immune cells, and these in turn are capable of communicating with nervous links through the secretion of a wide variety of cytokines. Powered managed therapeutic surface support system 100 may strengthen immune system, may lessen anxiety and stress, and may improve mood and behavior through its ability to relax the mental state of the user and trigger neuroendocrine activity. Relaxation, as defined in this disclosure, is a process that decreases the effects of stress on your mind and body. When stress is felt, the body responds by releasing hormones that can increase blood pressure and raise heart rate; this is called the stress response. Relaxation can help release these hormones and lower blood pressure and heart rate. Powered managed therapeutic surface support system 100 is physiologically therapeutic because it may be configured, through its combination of multidisciplinary devices and integrated systems to induce the user into a state of mental relaxation, strengthen the immune system, diminish stress, and improve mood and behavior in the user.

Referring now to FIG. 1, powered managed therapeutic surface support system 100 is described. Powered managed therapeutic surface support system 100 is designed for a concurrent physical and psychoneuroimmunological approach over a user, meaning the system aims to heal the user through both physical and psychological means. Powered managed therapeutic surface support system 100 combines a dual simultaneous approach 164 through a physical approach 168 and a psychoneuroimmunological approach 172. Dual simultaneous approach 164 is achieved herein through integrated system 104, mechatronic array 108, hardware 112, and software 116. Physical approach 168 is achieved through at least an independent main chamber 120, inductance sensor 124, first accessory chamber 128, second accessory chamber 132, first free-flow conduit 136, second free-flow conduit 140, and microcontroller 144. Psychoneuroimmunological approach 172 is achieved through fluid temperature control system 148, massage system 152, sound system 156, and motorized positioning system 160.

Still referring to FIG. 1, dual simultaneous approach 164 comprises integrated system 104, mechatronic array 108, hardware 112, and software 116. An "integrated system", in this disclosure, is a system of components that control mechatronic array 108 and in which hardware 112 and software 116 are embedded. In this disclosure, a "mechatronic array" is a device that may have fewer mechanical parts because of the integration of sensors, circuits, and motion components such as actuators. Mechatronics combines various disciplines in engineering, including mechanics, computing, control, and electronics, to build more reliable and less expensive machinery; circuits and other information technology components often aid in the precise control of such products. All components described herein in reference to FIG. 1 are components of the systems mechatronic array 108. Also in this disclosure, "hardware" is the physical part of a computer system, or in this case a microcontroller, which may include the case, central processing unit, monitor, mouse, keyboard, computer data storage, graphics card, sound card, speakers, and motherboard. Hardware 112 is configured to run software 116, which is the set of instructions that can be stored and run by hardware 112. Integrated system 104, mechatronic array 108, hardware 112, and software 116 are all referenced herein through the disclosure.

Still referring to FIG. 1, powered managed therapeutic surface support system 100 comprises physical approach 168, which comprises at least an independent fluid-filled main chamber 120. At least an independent fluid-filled main chamber 120 may be made of waterproof, flexible, extendable, and elastic material. In this disclosure, a "main chamber" refers to at least one cavity which houses a fluid, where the cavity directly receives the weight of a user. The main chambers are "independent" because they act individually from one another, meaning one main chamber does not interact with another main chamber. At least an independent fluid-filled main chamber 120 receives a user's body weight. At least an independent fluid-filled main chamber 120 may be located directly underneath the user; if some sort of bed frame, as explained below, is holding up the user, then at least an independent fluid-filled main chamber 120 may be located between the user and bed frame. At least an independent fluid-filled main chamber 120 may be adapted to enclose a variable amount and type of fluid between a lower support wall and a flexible upper support wall; flexible upper support wall is in direct contact with the body of the user. At least an independent fluid-filled main chamber 120 may be designed to contain a filling fluid. Filling fluids may include a liquid. Examples of liquids include but are not limited to water, liquids with a lower density than water such as an oil, or a combination thereof. Filling fluids may include a gas. Examples of gases include but are not limited to carbon dioxide, or any other gases that result from liquid biodegradation. When the gas is present, back pressure may be created, causing the need of removal of the gas. For this, filling-emptying valves are used, also acting as regulating valves for the gas outlet, not the liquid, and not the air inlet. With liquids, the advantage of managing its density and cost prevails. In an embodiment, filling-drainage valves may be included on at least an independent fluid-filled main chamber 120. The filling-drainage valves may also serve as regulating valves for the release of a gas. At least an independent fluid-filled main chamber 120 may be constructed of any flexible, strong material such as plastic, graphene, silicone, vinyl, or the like. Powered managed therapeutic surface support system 100 for pressure injuries may have at least one independent fluid-filled main chamber 120. At least an independent fluid-filled main chamber 120 may be the only chamber that receives the weight being supported from the user, is independent and transversely positioned to the user's body, and is designed to contain a variable amount and type of fluid depending on the weight of the body area it will support. Additionally, liners, such as those currently used in waterbeds, may be used to provide safe storage in the case of the accidental spillage of liquids, which may be detected by an electronic element that signals locally or remotely, if desired. A physical therapeutic approach over the user is made through the managed physical characteristics of the fluid-filled main chambers, in which the physical characteristics comply with the guidelines of the world authorities specialized in pressure injuries. World authorities specialized in pressure injuries includes the National Pressure Injury Advisory Panel (NPIAP), European Pressure Ulcer Advisory Panel (EPUAP), and the Pacific Pressure Injury Alliance (PPPIA); these authorities have created the "Clinical Practice Guidelines (CPG) for Prevention and Treatment of Pressure Ulcers".

Still referring to FIG. 1, at least an independent fluid-filled main chamber 120 may comprise an inductance sensor 124. In this disclosure, a "sensor" is a device that is configured to detect a phenomenon and transmit information related to the detection of the phenomenon. For example, in some cases a sensor may transduce a detected phenomenon, such as without limitation, voltage, current, speed, direction, force, torque, temperature, pressure, and the like, into a sensed signal. Inductance sensor 124 may include one or more sensors that may be the same, similar, or different. Inductance sensor 124 may include a plurality of sensors that may be the same, similar, or different. Inductance sensor 124 may include one or more sensor suites with sensors in each sensor suite being the same, similar, or different. Inductance sensor 124 may include any number of suitable sensors which may be efficaciously used to detect gap between the fluid and chamber walls. For example, and without limitation, these sensors may include a voltage sensor, proximity sensor, current sensor, multimeter, voltmeter, ammeter, electrical current sensor, resistance sensor, impedance sensor, capacitance sensor, a Wheatstone bridge, displacements sensor, vibration sensor, Daly detector, electroscope, electron multiplier, Faraday cup, galvanometer, Hall effect sensor, Hall probe, magnetic sensor, optical sensor, magnetometer, magnetoresistance sensor, MEMS magnetic field sensor, metal detector, planar Hall sensor, thermal sensor, and the like, among others. Inductance sensor 124 may include a small piece of metal in the upper wall of the chamber and may use the principle of electromagnetic induction to detect or measure objects. When an electrical current flows through an inductor a magnetic field is developed. Inductance sensor 124 may detect metallic objects that interact with this magnetic field, such as the small piece of metal, but non-metallic liquids do not interact with the magnetic field. Thus, inductance sensor 124 uses the sensor and metal to measure a predetermined gap between the level of fluid inside the chamber and the small piece of metal on the upper wall of the chamber. In other words, the predetermined depth limit of the water at a certain level. This gap serves to limit the maximum immersion of the user without touching the bottom of the main chamber. Inductance sensor 124 may be located outside and at the bottom of at least an independent fluid-filled main chamber 120. Inductance sensor 124 senses the body's immersion into the chambers with a preset limit level that prevents it from touching the lower part of the said chamber, thus optimizing the control of the managed physical characteristics. Inductance sensor 124 may be an electronic proximity device. In this disclosure, an "electronic proximity device" is a device configured to detect the movement or present location on objects without physical contact. An electronic proximity device may prevent the fluid from touching the lower part of the main chamber. Electronic proximity device may be in connection with a microcontroller 144. Electronic proximity device may limit the changes of the filling fluid inside the chambers which maximizes the control over the managed physical characteristics of managed powered managed therapeutic surface support system for pressure injuries 100. Inductance sensor 124 may be placed at the bottom and outside of the at least one independent fluid-filled chamber; it is configured to limit the vertical or volume variations of the first accessory chamber.

Still referring to FIG. 1, powered managed therapeutic surface support system 100 further comprises at least two corresponding accessory chambers connected to each main chamber. In this disclosure, an "accessory chamber" is a chamber fluidically connected to at least an independent fluid-filled main chamber 120. Plurality of accessory chambers are coupled to at least one independent fluid-filled main chamber 120. Plurality of accessory chambers comprises first accessory chamber 128 and second accessory chamber 132. Plurality of accessory chambers may further comprise an optional third accessory chamber positioned at an elevation below at least an independent fluid-filled main chamber 120.

Still referring to FIG. 1, at least an independent fluid-filled main chamber 120 may have a corresponding first accessory chamber 128 connected to it through a first free-flow conduit 136. First accessory chamber 128 possesses transfer power control to receive or return the filling fluid from said connected main chamber. In this disclosure, a "first accessory chamber" is an accessory chamber responsible for holding the fluid as it is removed and added to its respective independent main chamber. First accessory chamber 128 may serve to receive and return fluid displaced from the main chamber when a load, or the body of the user, is being supported and managed by the system. First accessory chamber 128 is configured to direct the filling fluid from first accessory chamber 128 to the at least an independent fluid-filled main chamber 120 and back to the first accessory chamber 128. First accessory chamber 128 may be similar in shape and material to at least an independent fluid-filled main chamber 120, a liquid pump, or any other component that can hold and transfer fluid. First accessory chamber 128 may exert the management of the physical characteristics of at least an independent fluid-filled main chamber 120 for the immersion and envelopment of the user for wider area of body contact, less pressure, and a more even distribution of pressure, which is explained more below with reference to FIG. 6. Powered managed therapeutic surface support system 100 is configured to adjust to changes in volume variation in the first accessory chamber 128 or a displacement of a relative vertical position of the first accessory chamber 128. Changes in the first accessory chamber's volume variation or the displacement of its relative vertical position exerts the management of the physical characteristics of the main chambers for pressure, immersion, and envelopment over the user. First accessory chamber 128 is fluidically connected to at least an independent fluid-filled main chamber 120 using first free-flow conduit 136. In this disclosure, a "free-flow conduit" is a channel or tube for conveying a fluid from one place to another and allows the fluid to move continuously without blockage. First free-flow conduit 136 may transport filling fluid into and out of at least an independent fluid-filled main chamber 120. First free-flow conduit 136 may be a of pipe or channel suitable for carrying fluids; the fluid may flow through first free-flow conduit 136 before entering the at least an independent fluid-filled main chamber 120 or first accessory chamber 128.

Referring still to FIG. 1, at least an independent fluid-filled main chamber 120 has a corresponding second accessory chamber 132 fluidically connected to the at least an independent fluid-filled main chamber 120 using second free-flow conduit 140. Second accessory chamber 132 may be empty of any fluid. Second accessory chamber 132 may be configured to dissipate any pressure from the at least an independent fluid-filled main chamber 120 since it is already empty of filling fluid. Second accessory chamber may be designed to be empty to dissipate any pulse or counterpressure from said main chamber, providing an always yielding performance to said main chamber and thus eliminating pressure points. Second accessory chamber 132 may be constructed of the same materials as the other chambers and may also be any shape as well, such as circular, tubular, rectangular, or the like. Unlike the other chambers, second accessory chamber 132 may be purposefully left empty. Second accessory chamber 132 may stay empty to yield to the pressure from at least an independent fluid-filled main chamber 120, causing dissipation of any pulse or counter-pressure. Second accessory chamber 132 may be fluidically connected to at least an independent fluid-filled main chamber 120 using second free-flow conduit 140. Second free-flow conduit 140 may be identical in material, shape, and size of first free-flow conduit 136, except that it may be attached to second accessory chamber 132 rather than first accessory chamber 128. Second free-flow conduit 140 may be any pipe or channel suitable for carrying fluids; the fluid may flow through second free-flow conduit 140 before entering the at least an independent fluid-filled main chamber 120. Second free-flow conduit 140 may be installed to disperse fluid from the at least an independent fluid-filled main chamber 120. Second free-flow conduit 140 may be fluid-filled to maintain a preset initial hydraulic head 204, which is further described below. Though second accessory chamber 132 mostly remains empty, it is possible that a negligible amount of filling fluid may flow into it despite the restriction from hydraulic head 204. However, second accessory chamber 132 still acts to relieve counterpressure from the load of the user's body in the at least an independent fluid-filled main chamber 120 to provide an always yielding performance to said main chamber and thus eliminating pressure injuries.

Still referring to FIG. 1, both first free-flow conduit 136 and second free-flow conduit 140 may comprise a bidirectional pump. In this disclosure, a "bidirectional pump" is a pump that allows flow of fluid in both directions, meaning the pump allows flow into a chamber and out of a chamber. Bidirectional pump comprises a hydraulic body comprising an inlet port which receives a fluid flow, a first outlet port and a second outlet port, and an impeller housed in said hydraulic body causing the fluid flow to move in either one direction or the other. Bidirectional pump in first free-flow conduit 136 may allow transfer of the fluid between at least an independent fluid-filled main chamber 120 and first accessory chamber 128. Bidirectional pump in second free-flow conduit 140 may allow transfer of the fluid between at least an independent fluid-filled main chamber 120 and second accessory chamber 132. Bidirectional pumps may possess the same amount of fluid as it moves throughout the chambers. As an example, the fluid output volume may be the same if not like the fluid input volume. Bidirectional pump may have two ports that both act as an inlet and an outlet since fluid flows in both directions. Bidirectional pump may help eliminate hydraulic shock, which, as used in this disclosure, is a pressure surge or wave caused when a fluid in motion is forced to stop or change direction suddenly. This pressure wave can cause noise and vibrations that may cause pipe rupture or collapse, which may result in further injury to the user's body when the bed is in use.

Still referring to FIG. 1, powered managed therapeutic surface support system 100 comprises psychoneuroimmunological approach 172. Psychoneuroimmunological approach 172 comprises fluid temperature control system 148, massage system 152, sound system 156, and motorized positioning system 160, all of which work together with physical approach 168 to achieve dual simultaneous approach 164. These systems are explained and described further herein with reference to FIG. 12.

Figure 2A:
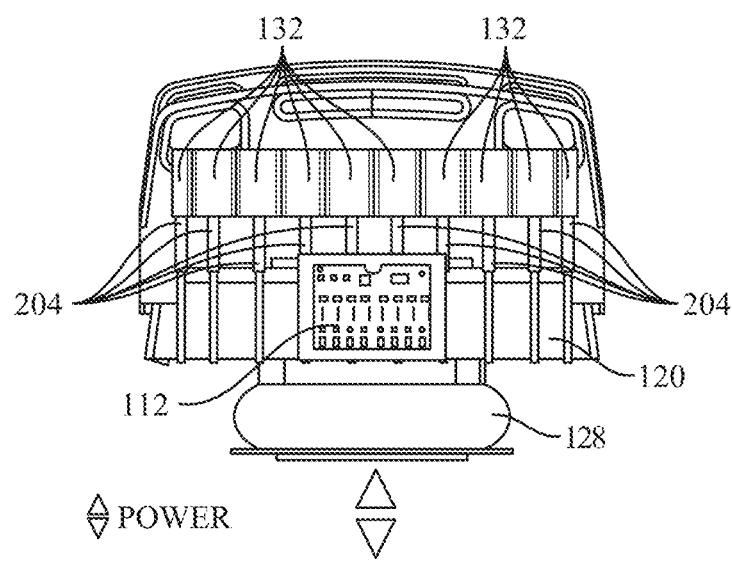
FIG. 2A shows the end view of an exemplary ten-main-chamber embodiment of the system.

Now referring to FIG. 2A, the end view of a possible ten-main-chamber embodiment of the powered managed therapeutic surface support system 100 is presented. Shown is hardware 112, which is further described in FIG. 11, at least an independent fluid-filled main chamber 120, first accessory chamber 128, second accessory chamber 132, and hydraulic head 204. Powered managed therapeutic surface support system 100 may include a bed frame. In this disclosure, a "bed frame" is an elevated structure used to hold and support the weight of powered managed therapeutic surface support system 100 and the user. Bed frame may also ease the user's ability to get in and out of the powered managed therapeutic surface support system 100. At least an independent fluid-filled main chamber 120 may be set side by side on the base of the bed frame where a normal mattress is usually placed. Underneath the layer of independent main chambers may be a layer of first accessory chambers 128. In this embodiment, each one may be connected to its own respective independent main chamber. Also visible from the end view of powered managed therapeutic surface support system 100 are second accessory chambers 132, which, like first accessory chambers 128, may be each connected to their own individual set of an independent main chamber.

Still referring to FIG. 2A, second free-flow conduit 140 comprises hydraulic head 204. A "hydraulic head" is, as used in this disclosure, a specific measurement of liquid pressure above a specific vertical datum inside the respective conduit. Hydraulic head 204 may be located at the part of the conduit that is closest and touching second accessory chamber 132. Hydraulic head 204 may be used to determine a hydraulic gradient between two or more points. Hydraulic head 204 may be initially preset to control the amount of initial pressure the filling fluid can possess. Hydraulic head 204 may be located at the part of the conduit that is closest and touching second accessory chamber 132. Additionally, hydraulic head 204 may also be vertical and non-collapsible. As used herein "non-collapsible" is defined as a conduit that is incapable of swelling or stretching under conditions of lower internal pressure relative to the pressure outside the conduit.

Figure 2B:
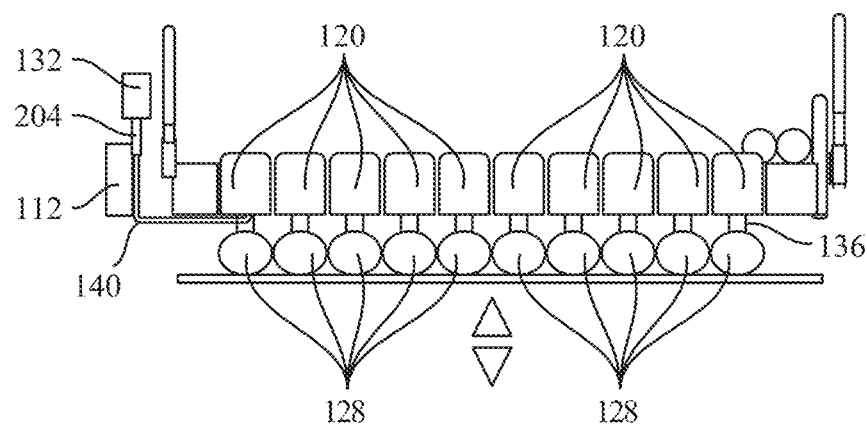
FIG. 2B shows the cross-sectional side view of an exemplary ten-main-chamber embodiment of the system.

Now referring to FIG. 2B, the cross-sectional side view representation of a ten-main-chamber embodiment of the system is shown. In this variation of the embodiment, end view components second accessory chambers 132, second free-flow conduits 140, and hardware 112 are seen from the side. Although located in this embodiment at the end, second accessory chambers 132, second free-flow conduits 140, and hardware 112 may be located anywhere in the system. Also, shown are first free-flow conduits 136 between the layer of at least an independent fluid-filled main chamber 120 and first accessory chambers 128.

Figure 2C:
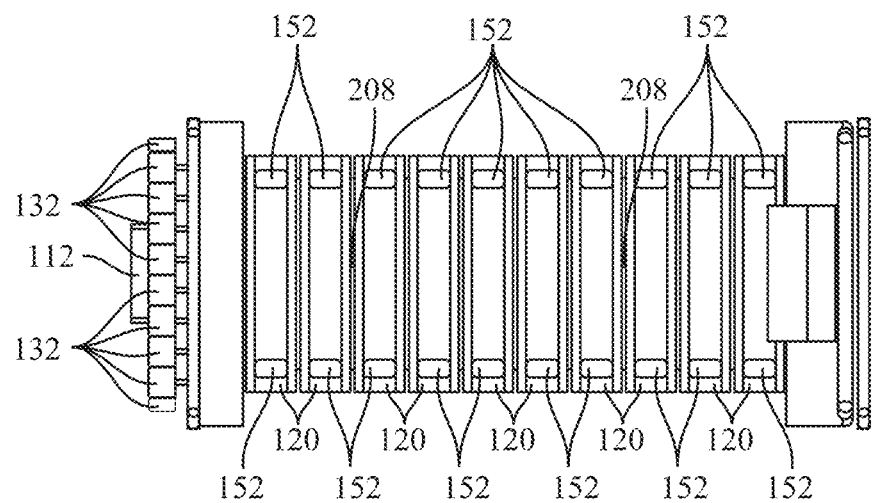
FIG. 2C shows the top views of an exemplary ten-main-chamber embodiment of the system.

Now referring to FIG. 2C, shown is the top views of a ten-main-chamber embodiment of the system. From the top, in this embodiment, at least an independent fluid-filled main chamber 120, second accessory chambers 132, and hardware 112 are visible. Additionally, hardware 112 controls specific multidisciplinary devices including a fluid temperature control system 148 that comprises fluid heaters 208. Fluid heaters 208 may be configured to control the temperature of the filling fluid inside the chambers. In this embodiment, a "fluid heater" is a piece of industrial heating equipment, used where only heat transfers are desired instead of pressure. Fluid heater may be a Calesco WB6403 LMF soft side with 170 watts of power. Fluid heater 208 may located beneath at least an independent fluid-filled main chamber 120. Fluid heater 208 may be waterproof. Fluid heater 208 may be communicatively connected to temperature sensor and further attached to at least an independent fluid-filled main chamber 120 to measure the temperature. Fluid heater 208 may be fully grounded, meaning, it is grounded into something to make it extremely stable, such as embedded into a bed frame, the ground, or another solid surface near the system. Fluid heater 208 may also include an insulated liquid-proof heating coil. A "heating coil" is coil of wire heated by the passage of an electric current and used for producing and maintaining a high temperature. Heating coil may be controlled with thermostat settings set by the user, or by predetermined settings. Fluid heaters 208 may comprise temperature sensors. Temperature sensors may be connected to microcontroller 144 (not shown). Temperature sensors may include thermocouples, thermistors, thermometers, passive infrared sensors, resistance temperature sensors (RTDs), semiconductor based integrated circuits (IC), a combination thereof or another undisclosed sensor type, alone or in combination. Temperature, for the purposes of this disclosure, and as would be appreciated by someone of ordinary skill in the art, is a measure of the heat energy of a system. Temperature, as measured by any number or combinations of sensors present within a sensor suite, may be measured in Fahrenheit (° F.), Celsius (° C.), or another scale alone or in combination. The temperature measured by temperature sensors may comprise electrical signals which may be transmitted to their appropriate destination wirelessly or through a wired connection. FIG. 2C also illustrates massage system 152, which is defined and described herein with reference to FIG. 12.

Figure 3:
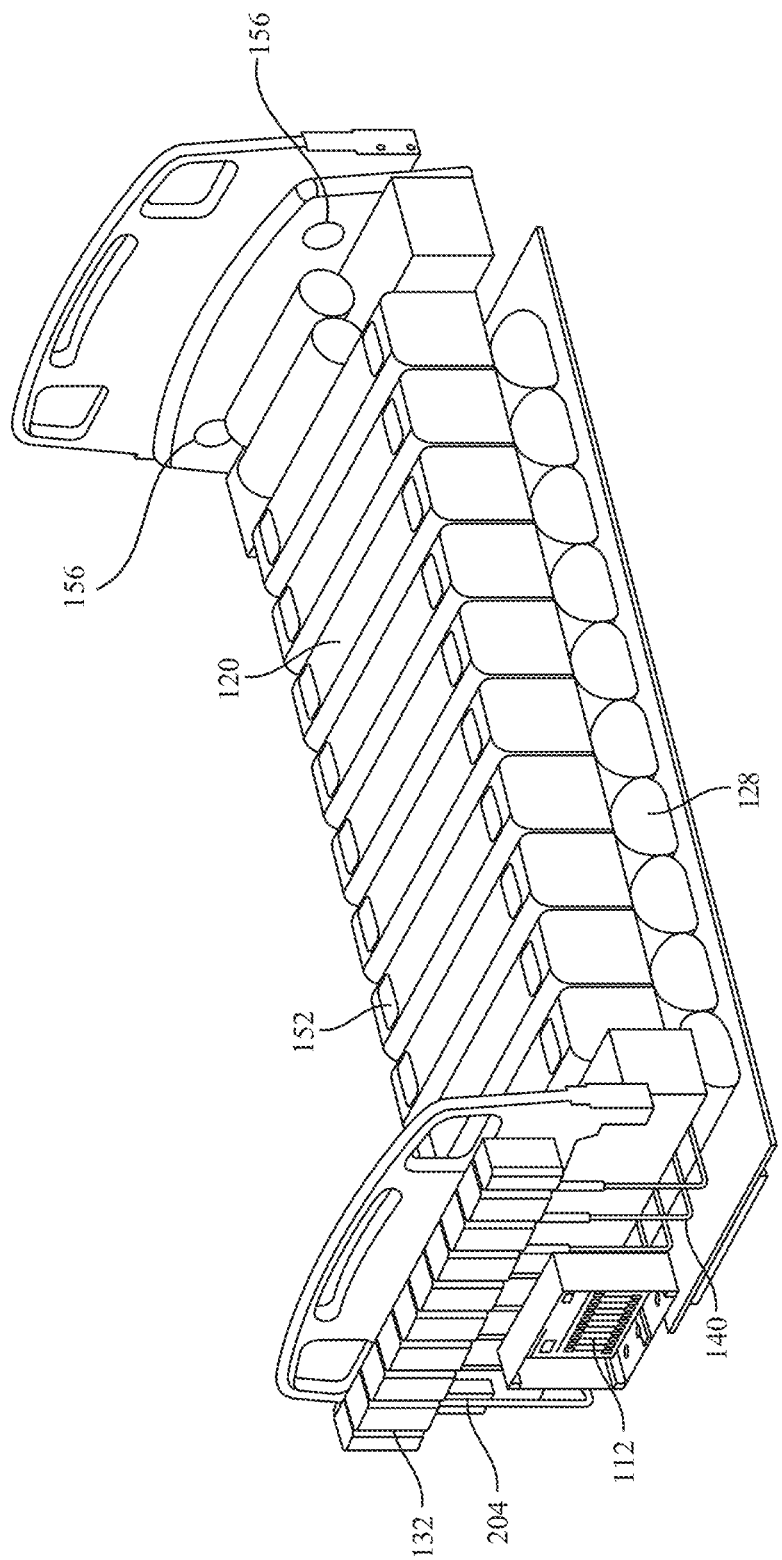
FIG. 3 shows the isometric view of the same embodiment as FIGS. 2A, 2B, and 2C.

Referring now to FIG. 3, the figure shows the isometric view of the same embodiment as FIGS. 2A, 2B, and 2C. Illustrated is the at least an independent fluid-filled main chamber 120 on a bed frame with a layer of first accessory chambers 128 located below the at least an independent fluid-filled main chamber 120. Then, second free-flow conduits 140 with hydraulic heads 204 connect at least an independent fluid-filled main chamber 120 to second accessory chambers 132. Both hardware 112 and massage system 152 are further described in FIGS. 11 and 12. Additionally, in an embodiment, sound system 156 is shown through speakers located on either side of where the head of the user rests; sound system 156 is explained further herein with reference to FIG. 12.

Figure 4:
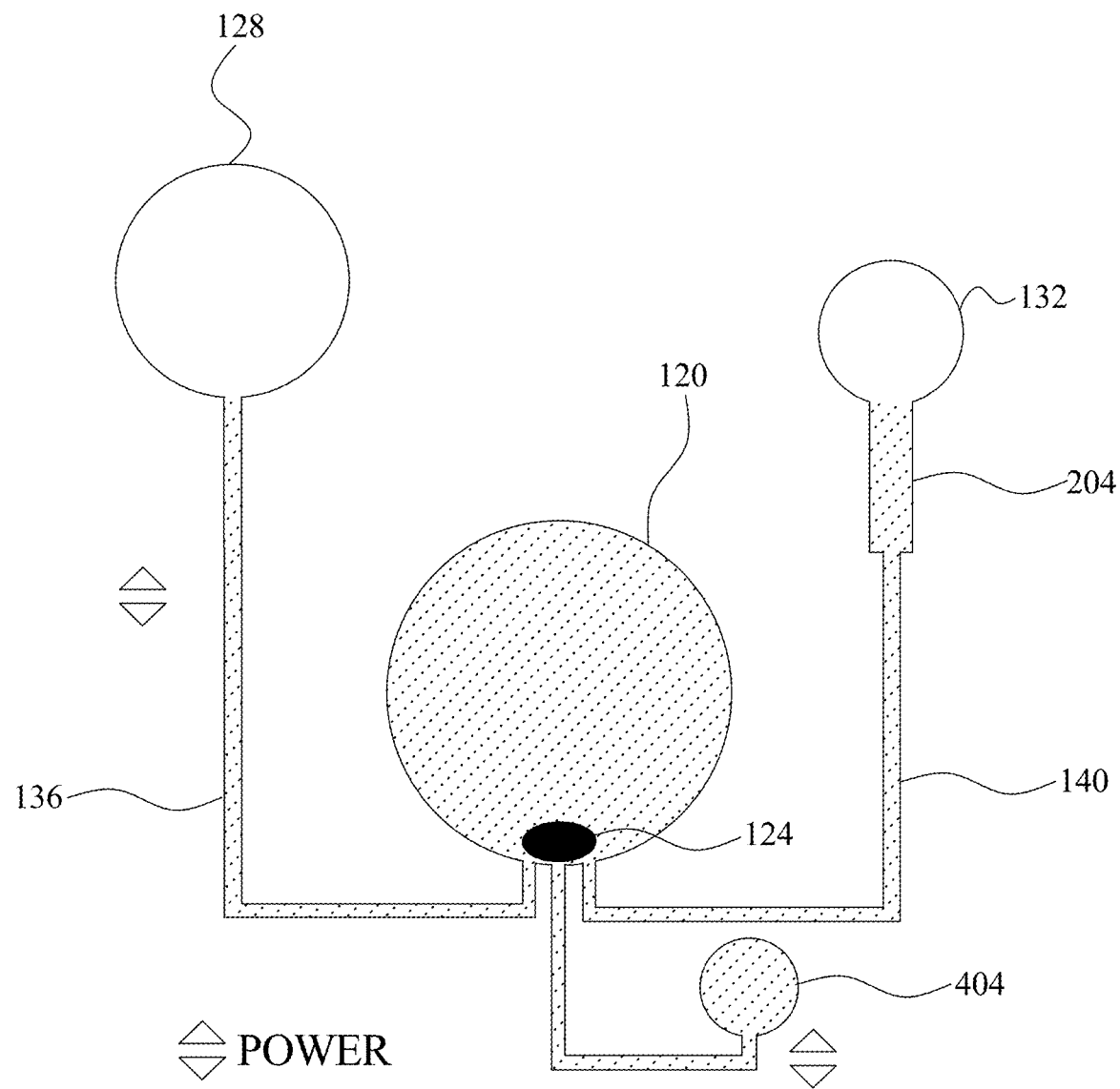
FIG. 4 is a schematic vertical cross-section showing an exemplary relative arrangement of the chambers of the system.

Referring now to FIG. 4, an exemplary schematic, vertical cross-section showing the relative arrangement of the chambers of a powered managed therapeutic support surface system 100 is illustrated. At least an independent fluid-filled main chamber 120, inductance sensor 124, first accessory chamber 128, first free-flow conduit 136, second accessory chamber 132, second free-flow conduit 140, hydraulic head 204, and optional third accessory chamber 404 are shown. The dots inside the chambers represent the level of filling fluid.

Still referring to FIG. 4, plurality of accessory chambers may further comprise an optional third accessory chamber 404 positioned at an elevation below the at least an independent fluid-filled main chamber 120. Optional third accessory chamber 404 is configured refill and maintain the filling fluid volume in the at least an independent fluid-filled main chamber 120. Optional third accessory chamber 404 may be connected and arranged at a lower elevation than the at least an independent fluid-filled main chamber 120. Optional third accessory chamber 404 may be used to refill fluid in the main chamber if the fluid is reduced or removed due to the release of gas during biodegradation; causing the need for refilling of fluid volume in the main chamber for the system to continually support the user. Optional third accessory chamber 404 may be made of the same materials as the other chambers and may also be any shape as well, such as circular, tubular, rectangular, or the like.

Still referring to FIG. 4, hydraulic head 204 is located above at least an independent main chamber 120 and may be filled with fluid to maintain a preset initial hydraulic head 204. Additionally, second accessory chamber 132 remains empty of filling fluid to relieve pressure from at least an independent main chamber 120, thus eliminating pressure points and eliminating the appearance and recurrence of a pressure injury.

Figure 5:
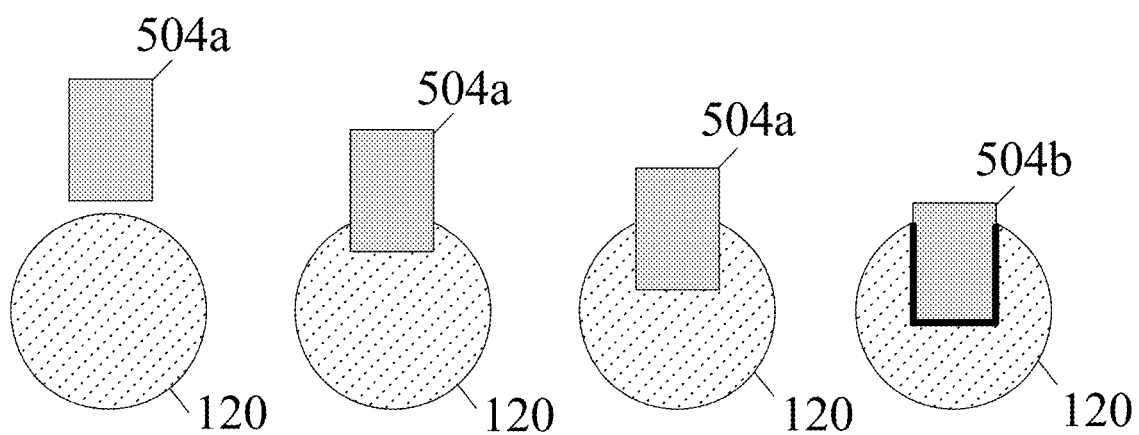
FIG. 5 illustrates the process of immersion or envelopment of the load inside the main chamber.

Now referring to FIG. 5, illustrated is process of immersion 504a or envelopment 504b of the load inside the main chamber. Shaded block represents the body of a user. Moreover, a larger area is used to reduce pressure on a bony prominence of the user. Immersion and envelopment are the phenomena that produce a reduction in pressure at a bony prominence. Immersion refers to the depth of penetration, or sinking, into a support surface. Envelopment refers to the ability of a support surface to conform, so to fit or mold around irregularities in the body and is further explained below. The dotted filling inside the figure represents the level of the filling fluid. In this disclosure, the "load" may refer to the weight of the user's body on top of the at least an independent fluid-filled main chamber 120. Load adds pressure from above to at least an independent fluid-filled main chamber 120. Since filling fluid conforms to the shape of the area it is contained to, which in this disclosure is at least an independent fluid-filled main chamber 120, and at least an independent fluid-filled main chamber 120 take the load of the user, sinking of the mass, in this case the user's body, occurs, as immersion 504a. Also, envelopment 504b represents a fluid's ability to conform to the irregularities of the load contour. Once the load of user's body is applied on top of at least an independent fluid-filled main chamber 120, envelopment 504b of the body of the user occurs. Powered managed therapeutic surface support system 100 for pressure injuries achieves such envelopment primarily through regulating the contained fluid volume of the filling fluid of independent main chamber 120. This allows the load to sink at will or possibly automatically and, by reaching a controlled immersion 504a and envelopment 504b, increasing the area of contact to the maximum. Natural, ample, and perfect body-contour contact with the user is achievable, thus making the pressure optimal to ensure that the pressure stays at a minimum and is evenly distributed. The adaptability of the main chamber to fill with liquid and contour the human body produces an almost liquid-to-liquid contact since the body of a user can be sixty percent liquid water, thus creating maximum immersion 504a, envelopment 504b, and support. The lateral and lower contact, or envelopment 504b exerts an optimum touch on all sides which, in turn, contributes to a reduction and even distribution of body pressure over large areas of the user's body.

Figure 6A:
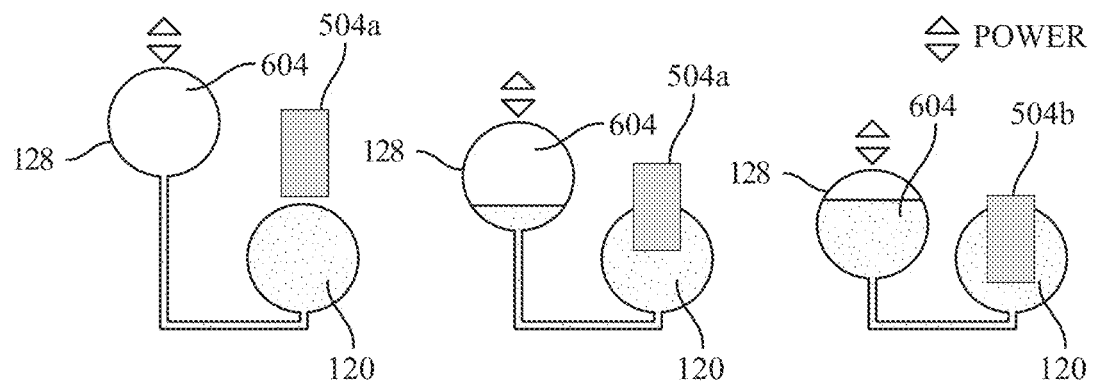
FIG. 6A shows the management of immersion and envelopment of the load depending on the vertical variations of the first accessory chamber.
Figure 6B:
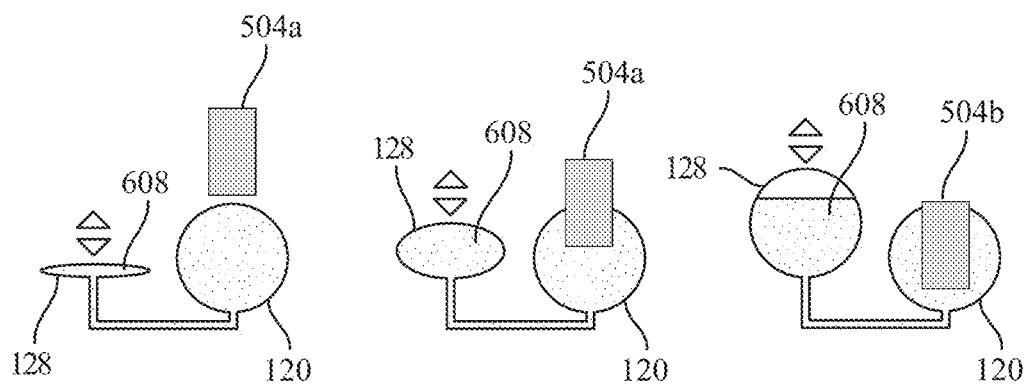
FIG. 6B shows the management of immersion and envelopment of the load depending on the volume variations of the first accessory chamber.

Now referring to FIGS. 6A and 6B, FIG. 6A shows the management of the physical characteristics of immersion 504a and envelopment 504b of the load into at least an independent fluid-filled main chamber 120, depends on the vertical position variation 604 of first accessory chamber 128. The management of immersion 504a and envelopment 504b of the load depending on the vertical position variation 604 of the powered fluid first accessory chamber 128 or volume is shown. Management of the load depends on the vertical position variation 604 and volume variation 608 in FIG. 6B for first accessory chamber 128. As immersion 504a and envelopment 504b occur, first accessory chamber 128 may be lowered, thus decreasing the vertical position to allow filling fluid to enter first accessory chamber 128 from at least an independent fluid-filled main chamber 120. Thus, the downward vertical position variation 604 of the first accessory chamber 128 with respect to the at least an independent-fluid-filled main chamber 120, as it descends, takes liquid from the at least an independent-fluid-filled main chamber 120 and the user's body sinks, controlled by the vertical position variation 604 of the first accessory chamber 128, the which in turn is limited to its maximum downward variation by the inductance sensor 124. Also, as mentioned above, the dotted filling inside the figure represents the level of the filling fluid and the shaded block represents the body of a user.

Still referring to FIGS. 6A and 6B, FIG. 6B illustrates the management of the physical characteristics of immersion 504a and envelopment 504b of the load into at least an independent fluid-filled main chamber 120, depends on the volume variation 608 of first accessory chamber 128. Volume variation 608, as used in this disclosure, is the change in the volume of the first accessory chamber. As volume variation 608 expands, fluid is withdrawn from the main chamber 120 and a controlled sinking of the body of the user is achieved. As immersion 504a and envelopment 504b occur, first accessory chamber 128 may increase its volume, thus allowing more space to hold fluid from at least an independent fluid-filled main chamber 120.

Figure 7:
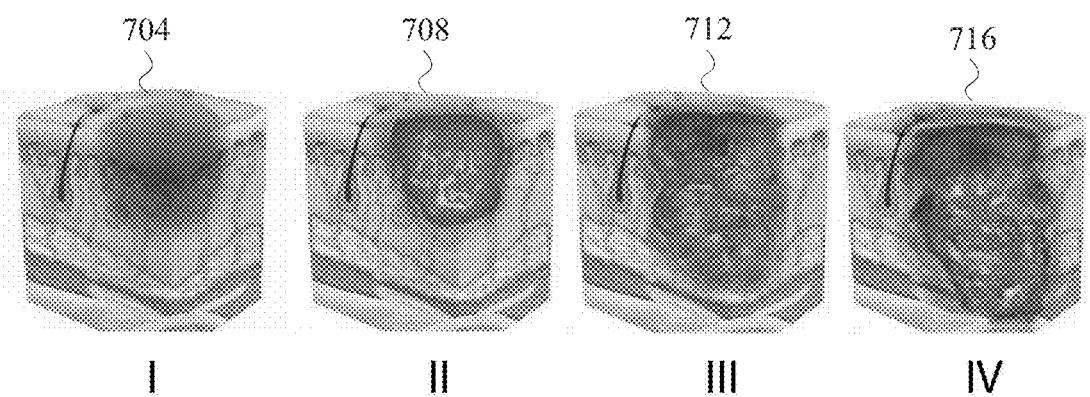
FIG. 7 is a diagram exemplifying the four stages of a pressure injury on the skin of a user.

Now referring to FIG. 7, four stages of the development of pressure injuries are exemplified. The system explained above help physically reduce the presence of pressure injuries in a user. A "pressure injury" can also be referred to as a bedsore, pressure ulcer, pressure sore, or decubitus ulcer; it is an area of injured skin. Pressure injuries happens when force is applied on the surface of the skin. This force can be a constant pressure on an area of skin or a dragging (shearing) force between the skin and another surface. The stages of pressure injuries describe the severity of the wound. In stage I 704, the skin becomes discolored and may appear red in those with lighter skin tones or blue/purple in users with darker skin tones. Unlike other areas of the skin, at this stage I 704, skin affected does not blanch, or turn white, when pressed with a finger. At stage II 708, the superficial damage of the user's skin begins to show. The top layer of the skin may be lost, and the wound may resemble a blister. However, if pressure is taken off the wound at this stage II 708, the top layer of skin is able to repair itself to recovery. If the injury is not treated at stage II 708, then stage III 712 occurs. Stage III 712 represents a deeper, open wound extending into the fatty layer of the skin without the appearance of muscles and bone. If symptoms continue to occur and the wound develops down to the user's bone or muscles, then the most severe stage IV 716 has been reached. Injuries in stage IV 716 are not only prone to further infection but may be life-threatening. The invention explained herein allows for the reduction of pressure in the support chambers in the affected zones. It delegates the bodily support to the adjacent chambers which, given their permanent ease of free flow, absorb the weight of the user, thus eliminating extreme pressure in zones that are prone to pressure injuries.

Figure 8A:
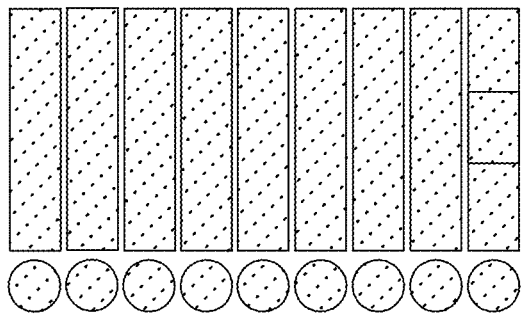
FIG. 8A shows a bird's eye view of an exemplary embodiment of the independent fluid-filled main chambers.

Now referring to FIG. 8A, shows a bird's eye view of another exemplary embodiment of the independent fluid-filled main chambers. Here, the dots represent the fluid is inside the chambers. Direct applications of the present invention to the treatment of pressure injuries are shown in FIG. 8A, where preventive use does not require a more significant variation of a standard support surface provided by this innovation designed to avoid formation and recurrence of pressure points.

Figure 8B:
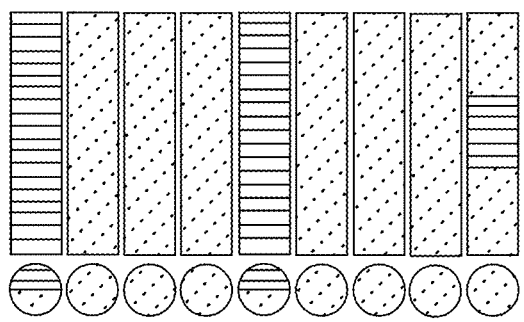
FIG. 8B shows a bird's eye view of another, second exemplary embodiment of the independent fluid-filled main chambers.

Now referring to FIG. 8B, another bird's eye view of an exemplary embodiment of the chambers wherein a more significant variation of the liquid inside the chambers is shown. In the case of latent risks, such as the mentioned areas of higher incidence explained below, the at least an independent fluid-filled main chamber 120 of said areas could be partially filled with a liquid of lower density; this will further improve the yielding benefits of the present invention on at least an independent fluid-filled main chamber 120. In this embodiment, the dots once again represent filling fluid, however the horizontal patterned areas represent the chambers filled with an adjusted filling fluid, which may include a combination of fluids such as oil and water. This combination is to aid in specifically relieving pressure in the common areas of high incidence for pressure injuries as explained below in FIG. 9.

Figure 8C:
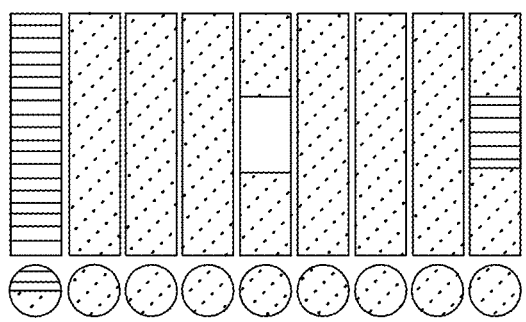
FIG. 8C shows a bird's eye view of another, third exemplary embodiment of the independent fluid-filled main chambers.

Now referring to FIG. 8C, another bird's eye view of an exemplary embodiment of the chambers is shown. The combination of oil and water used in the chambers supports the user' head and feet. The empty chamber may represent a chamber with no filling fluid at all to help compensate for the higher possibility of pressure injuries occurring in that area. In the case of the presence of pressure injuries at stages III and IV from FIG. 7, it is advisable to avoid any contact with the surface. This disclosure allows for the reduction in the size or the partial elimination of the support chambers in the affected zones, delegating the body support to the adjacent chambers, which, given their permanent ease of free flow, absorb the weight unsupported by the avoided contact and thus facilitate the application of present known therapeutic measures.

Figure 9:
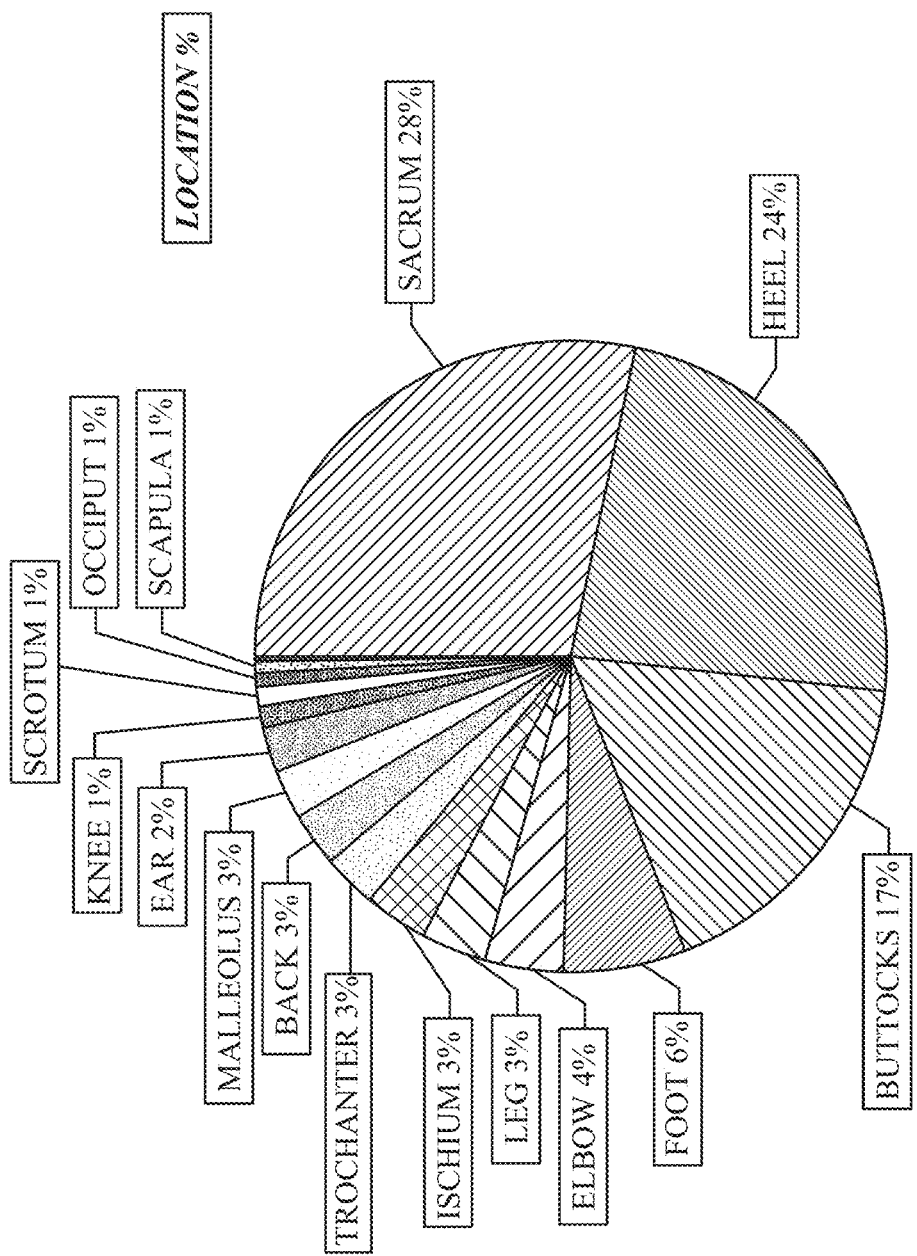
FIG. 9 is an exemplary pie chart illustrating the probability of common areas of a user's body where pressure injuries may develop.

Now referring to FIG. 9, an exemplary pie chart illustrating the probability of common areas of a user's body where pressure injuries may develop is illustrated. In this figure, a body area is shown next to a percentage, which represents the likelihood of pressure injury occurring in that area. Statistics are vital when fighting pressure injuries. As shown, a high incidence of 75% is located in only four spots on the human body: sacrum 28.3%, heel 23.6%, buttocks 17.2%, and foot 6.2%, and all of them in only two zones: the central and lower parts of the body as boxed out in FIG. 10. The present disclosure targets treatment in these four areas, as well as all other areas of the body, through the use of the chambers as explained earlier in this disclosure.

Figure 10:
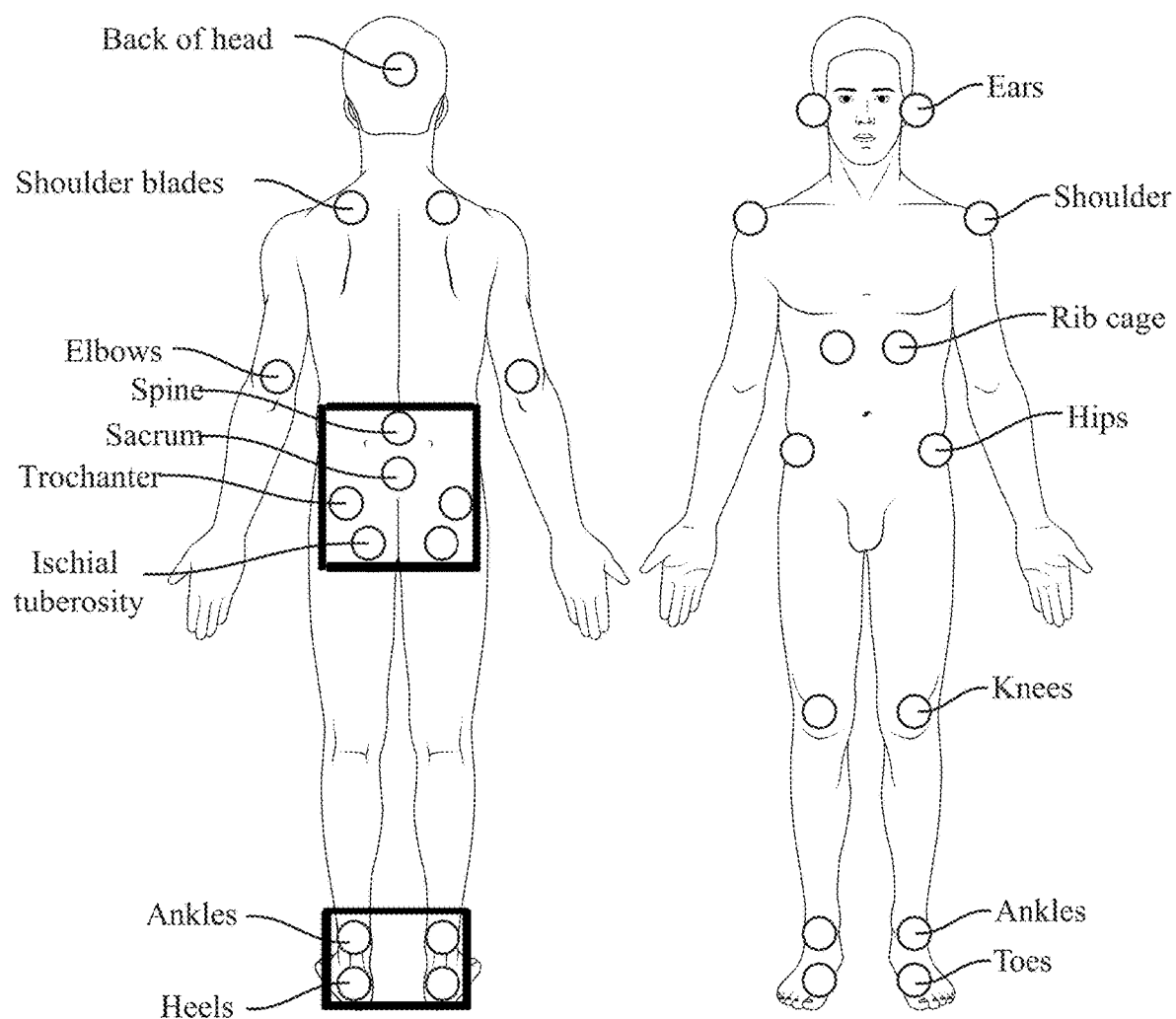
FIG. 10 is an exemplary diagram illustrating the common areas of a user's body where pressure injuries may develop, including boxes showing the most recurring areas.

Now referring to FIG. 10, an exemplary diagram pointing out the common areas of a user's body as described in FIG. 9. As said above, a high incidence of 75% is located in only four spots on the human body: sacrum 28.3%, heel 23.6%, buttocks 17.2%, and foot 6.2%, and all of them in only two zones: the central and lower parts of the body seen inside the boxes in the figure. These spots represent the areas of the body that the present disclosure focuses on when treating the injuries.

Referring now back to FIG. 1, hardware 112 is based on the use of one or more microcontrollers 144 electronically connected to the at least an independent fluid-filled main chamber 120. Microcontroller 144 may be embedded with its own hardware and software designed to control a mechatronic array operating simultaneously with an integrated system in a convergent manner. Microcontroller 144 may include any sort of computing device. Computing device may include any computing device as described in this disclosure, including without limitation a microcontroller, microprocessor, digital signal processor (DSP) and/or system on a chip (SoC) as described in this disclosure. Computing device may include STM32F407VGT6/package LQFP100. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Microcontroller 144 as well as its hardware and software are explained further herein with reference to FIGS. 1, 2, and 11. Hardware 112 may include microcontroller 144.

Now referring back to FIGS. 2A, 2B, 2C, and 3, hardware 112 is shown in an embodiment of powered managed therapeutic surface support system 100. Microcontroller 144 may be the physical part of hardware 112 and may be located anywhere on the system. Microcontroller 144 may be communicatively connected to fluid temperature control system 148, massage system 152, sound system 156, and motorized positioning system 160. Microcontroller 144 may also be communicatively connected to any other components of the system described herein, including the chambers and conduits. Microcontroller 144 may be configured to receive a temperature reading from the temperature sensors attached to fluid heaters 208 and transmit it to microcontroller 144. Microcontroller 144 may then determine a temperature adjustment and transmit that to the fluid heater to alter temperature of filling fluid. Microcontroller 144 then may adjust the temperature of at least an independent fluid-filled main chamber 120 using fluid heater 208 as a function of the temperature reading. Microcontroller 144 may also receive a user-desired temperature from a user device, meaning that the user can choose the temperature of the fluids inside the chambers. The temperature control system and other systems are further described herein with reference to FIG. 12.

Figure 11:
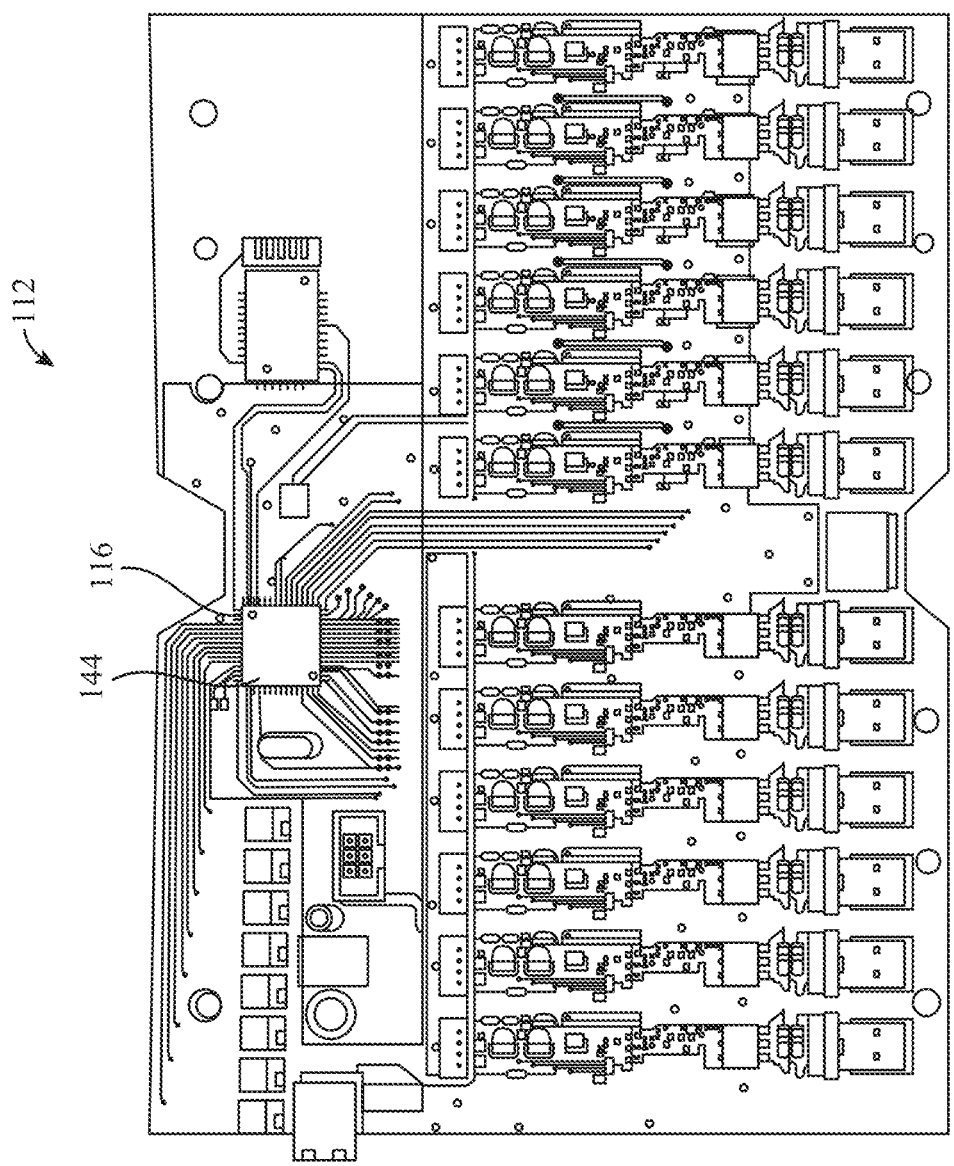
FIG. 11 illustrates the hardware designed to manage the multiple functions and accessories of the system.

Referring now to FIG. 11, shown is a close-up of hardware 112 designed to manage the multiple functions and accessories of the powered managed therapeutic support surface system. Hardware 112 may include microcontroller 144 where a software 116 may be stored. Software 116 may include a sequence of instructions for microcontroller 144 programmed into a suitable graphic user interface, such as a touch screen, in communication with microcontroller 144 to control elements of powered managed therapeutic surface support system 100. The psychoneuroimmunological therapeutic approach of powered managed therapeutic surface support system 100 over the user comprises simultaneously operating specific multidisciplinary devices paired with the integrated system 104 that are selected to induce the user into a relaxed mental state; hardware 112 may use microcontroller 144 to operate these specific multidisciplinary devices. Specific multidisciplinary devices may include a fluid temperature control system, massage system 152, a sound system 156, and motorized positioning system 160. Hardware 112 also may comprise a software based on microcontrollers, where the software further explained below.

Figure 12:
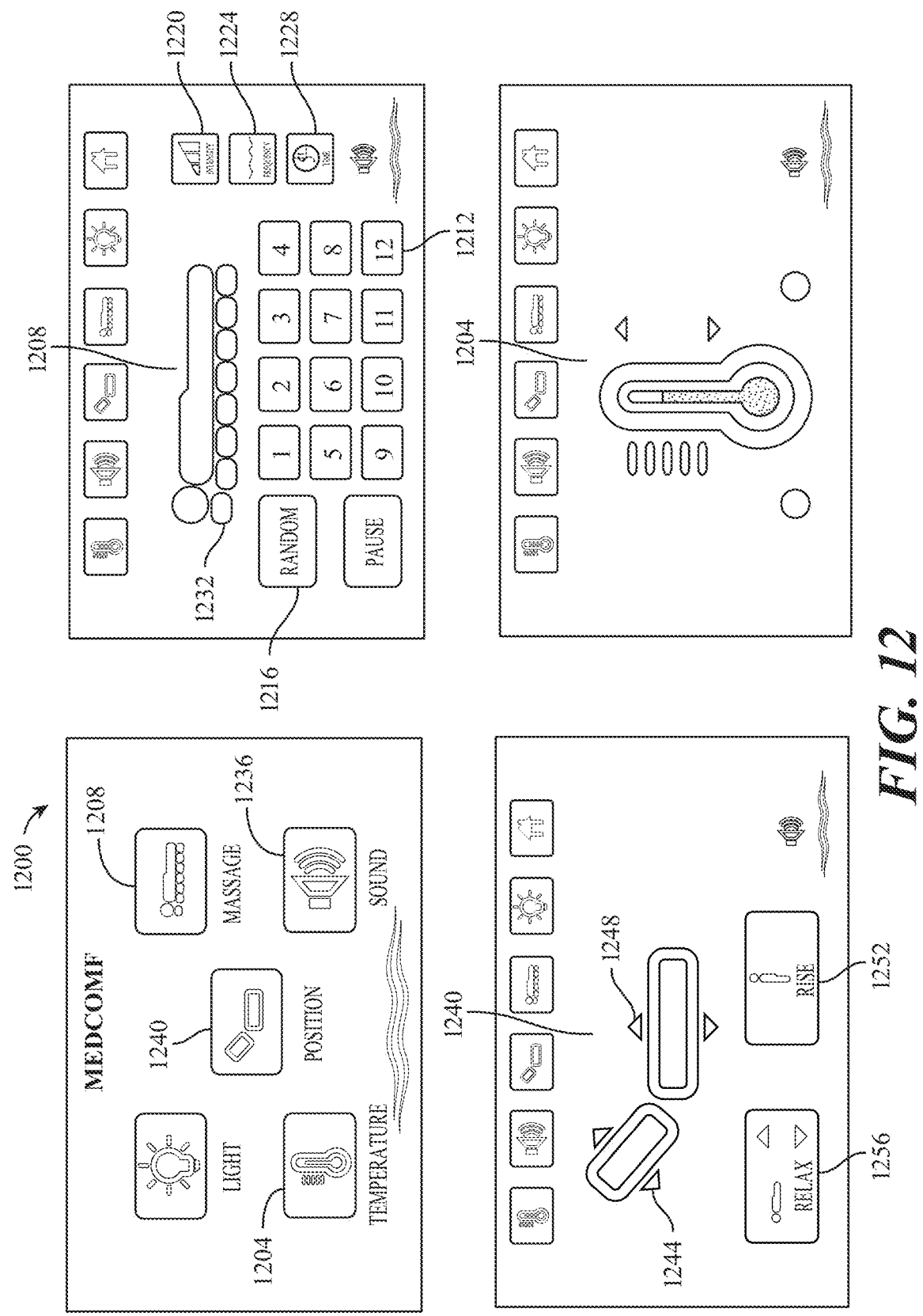
FIG. 12 shows an exemplary graphic user interface presented on a touch screen panel according to a preferred embodiment of the system.

Referring now to FIG. 12, software program of powered managed therapeutic surface support system 100 comprises a touch screen mobile coupled to said integrated system 104 and adapted to permit the user to monitor and adjust the specific devices of the system. Touch screen further comprises an IOT connection, including Bluetooth and Wi-Fi, in said touch screen mobile to facilitate local and remote control of the different device of the integrated system 104 and the user itself. To stablish interaction between the microcontroller and the mobile, the MAC address of the Bluetooth module is obtained to connect with the mobile application. Once connected, a different command is added to each button to identify it and send that command to the microcontroller. The microcontroller is programmed so that, when it has data in the buffer, it activates an interrupt and processes the received data. Software program is configured and stored in the embedded microcontroller to manage the temperature across various zones, perform different massages, play audio, and positioning the body the user. Software program is configured to manage the said surface pressure, said immersion, and said envelopment of the user, for said concurrent physical and psychoneuroimmunological therapeutic approach.

Still referring to FIG. 12, software 116 displayed through a screen of an exemplary suitable graphic user interface/device is disclosed. In this disclosure, a "user device" refers to a device designed to interact with a user and receive information from the user. The embodiment shown of a user device is a touch screen panel. User device may be communicatively connected to microcontroller 144 and configured to receive user inputs associated with operating parameters of the system. Software program may be configured to control operating parameters. User device is configured to permit a user to monitor and adjust operating parameters. In this disclosure, "operating parameters" are the specifications of the system that are required for operation. Operating parameters for powered managed therapeutic surface support system 100 may include temperature, pressure, reclination of a support pad, initiation of massage components, or the like. Operating parameters may also include a predetermined firmness of the flexible upper support surface of at least an independent fluid-filled main chamber 120. Software 116 in user device may also be configured to perform a plurality of therapeutic functions on the user. Software 116 is exemplified through screen system 1200.

Now referring back to FIG. 1, software 116 is configured to control a plurality of relaxation components. Plurality of relaxation components includes a fluid temperature control system 148, a massage system 152, a sound system 156, and a motorized positioning system 160.

Referring to FIG. 12, software 116 may include a fluid temperature control system 148 controlled through temperature control 1204. Fluid temperature control system 148 may be attached to fluid heaters 208 and temperature sensors to regulate and change filling fluid temperature. Fluid heater 208 may be fully grounded and insulated liquid proof heating coil with thermostat setting and is controlled at will by the user or automatically at a preset temperature level. Fluid temperature control system 148 is a system used to control the temperature of the filling fluid inside of the chambers. For safety measure, the fluid temperature control system 148 may not exceed 42 degrees Celsius. Fluid temperature control system 148 may also use a standard thermostat and snap setting with various levels of temperature for user selection. Fluid temperature control system 148 may include a Calesco WB6403 LMF soft side with 170 watts heater. Further, the integrated system may have two additional temperature sensors, the first at the points of contact between the user and the at least an independent fluid-filled main chamber 120, with five levels of temperature control for user choice, and the second sensor on the heater itself, limiting its maximum temperature to 42 degrees Celsius, as extra safety measure, avoiding injury to the skin of the user even with no presence of fluid.

Still referring to FIG. 12, software 116 may include a massage system 152 controlled through massage control 1208. Massage system 152 is a system used to manipulate the soft tissues of the user to relieve pressure and for the purpose of relaxation. Massage system 152 comprises multiple points of pulsating fluid; this is done by using vibrating eccentric micromotors controlled by the user through a selection of programs, intensity, frequency, time, and active zones. Vibrating eccentric micromotors may also send vibrations through the filling fluids to manipulate the soft tissues of the user. Massage system 152 may have the ability to control a selection of twelve programs 1212 and a random mixer 1216. Each may have three levels each of intensity 1220, frequency 1224, and time 1228 for a massage. Massage system 152 may also have selectable active zones 1232 to avoid massage on the pressure injuries critical or affected areas. Massage system 152 activates blood and lymph circulation, improves cellular health, tissue functions more efficiently, and diminishes swelling. It also reduces painful muscle contractions and spasms, all focused on the care of the user and their mental relaxation process.

Still referring to FIG. 12, software 116 may also include a sound system 156 controlled through sound control 1236. Sound system 156 is a system used to play different sounds to the user and may be configured to play music to engage the attention of the user. Sound system 156 may be configured to play music or any sort of sound that fosters relaxation in the user. Sound system 156 may be used to transport the user's mind to a state of relaxation. Sound system 156 comprises smart stereo speakers paired with the integrated system for streaming connection to play pre-programmed lists of sounds to engage the attention of the user. "Streaming" may be done through the user of an Internet of Things, explained below. Pre-programmed lists are pre-set in order to transport the mind of the user to a state of relaxation. Sound system 156 may be its own device or can be a part of user device. Sound system 156 may be connected to another form of music software to connect to the audio. Sound system 156 may include Bose Bluetooth Soundlink.

Still referring to FIG. 12, software 116 may also include at least one motorized positioning system 160 is also included and controlled by position control 1240. At least one motorized positioning system 160 may be configured to place a backrest of the user for maximum comfort and mind relaxation. Motorized positioning system 160 may be used to adjust the angle of the user's backrest 1244 and the height of the support pad 1248, including buttons to help the user rise and exit 1252, or to control the softness of the support pad 1256. For example, a user may use a touch screen device attached to powered managed therapeutic surface support system 100 and adjust the firmness of powered managed therapeutic surface support system 100, which entails manipulating the amount of filling fluid in at least an independent fluid-filled main chamber 120 since they come into direct contact with a user. Motorized positioning system 160 may include linear actuators. Linear actuators may include Linak LA31 IPX6 Careline for medical applications, Jiecang JC35EN-3A 6000N IPX6 medical line, or the like. Motorized positioning system 160 may include a back-positioning system with two synchronized linear actuators employed for the desired comfort of the user and attain said mental state of relaxation. Motorized positioning system 160 may include a raising-lowering function of the support surface with two columns, each with three stages of synchronized linear actuators, to facilitate the activity of the medical practitioners as much as the exit of the user. Motorized positioning system 160 also may include a relax function to influence the immersion, envelopment, softness, and pressure of the said main support surface; Baselifts designed for synchronized variations in height are employed, allowing variations in the volume of the corresponding first accessory chamber. When the user lies on the main chambers, the body of the user adopts an enhanced, transversal position with weight distributed in each zone; this position is exactly maintained during all fluid movements that are made. Motorized positioning system 160 also may include a raise function performed by a preprogrammed sequence. The fluid may be returned from the first accessory chamber 128 to the at least an independent fluid-filled main chamber 120 using these said Baselifts, for better support of the user when getting out of bed. Then, the bed is lowered by lowering columns and a backrest system is elevated to help the user to leave the bed. After a predetermined time, the backrest may return to its horizontal position.

Still referring to FIG. 12, software 116 may be configured to communicate with a central network. In some embodiments, microcontroller 144 may be configured to directly communicate with central network. In some embodiments, software 116 may be configured to directly communicate with central network through a cellular, GPS, and/or Wi-Fi connection. In some embodiments, powered managed therapeutic surface support system 100 may include a plurality of software programs and/or a plurality of microcontroller 144. In some embodiments, a plurality of microcontrollers 144 may be configured to communicate with a central network. In other embodiments, microcontroller 144 may communicate with nearby computing devices that may be configured to forward any data from microcontroller 144 to central network. In some embodiments, a communication between microcontroller 144 and a computing device of another powered managed therapeutic surface support system 100, which may include a background connection. A background connection may include a form of connection that may require no action from a carrier to establish a communication between microcontroller 144 and a computing device of another system. In some embodiments, microcontroller 144 may include a foreground connection. A foreground connection may include a form of connection that may require an action to establish a connection between a computing device of another system and microcontroller 144. In some embodiments, a background connection may include microcontroller 144 passively connecting to the Internet of Things ("IoT"). The "Internet of Things" as used throughout this disclosure describes a network of physical objects embedded with sensors, software, and/or other technologies for connecting and exchanging data with other device and systems over the internet. A passive connection to the Internet of Things may include microcontroller 144 receiving transmission from other computing devices without actively searching for those computing devices. In some embodiments, microcontroller 144 may actively connect to the Internet of Things. Actively connecting to the Internet of Things may include microcontroller 144 sending search signals to locate other computing devices. In some embodiments, microcontroller 144 may transmit search signals in timed intervals. In some embodiments, a plurality of computing devices may be configured to connect to microcontroller 144. In a non-limiting example, a plurality of Bluetooth and/or Wi-Fi-enabled beacons may be configured to connect to microcontroller 144. A plurality of beacons may include small computing devices that may be placed at key locations. In some embodiments, a plurality of beacons may be placed in a plurality of transportation units, such as, but not limited to, cars, trucks, ships, boats, motorcycles, planes, drones, bicycles, and the like. In other embodiments, microcontroller 144 may be configured to connect to already existing computing devices, such as but not limited to, smartphones, laptops, desktops, tablets, and the like. In some embodiments, the Internet of Things may include already existing computing devices without the need for beacon placement. In some embodiments, a foreground connection may include scanning a QR code. In some embodiments, a foreground connection may include connecting microcontroller 144 to a computing device through a Bluetooth connection. In some embodiments, a foreground connection may include connecting microcontroller 144 to a computing device through a Wi-Fi connection. Another computing device may be configured to interact with an application, web browser, and the like. Interaction of an application and/or web browser may include interacting with a GUI of a computing device. In some embodiments, an application and/or web browser may be configured to share data between microcontroller 144 and another computing device. In some embodiments, an application and/or web browser may be configured to communicate data to central network. The therapeutic user support surface is configured to treat pressure injuries and simultaneously create an integrated physical and psychoneuroimmunological therapeutic approach to treatment. The plurality of chambers and microcontroller are designed to physically treat and prevent pressure injuries to the user while the hardware and software program work to psychologically create a relaxing and comfortable environment for the user. The mechatronic array is assembled in a solid structure with multidisciplinary electric and electronic elements, varied sensors, and multiple synchronized linear actuators, and wherein the mechatronic array performs the raising or lowering the support surface. Software may provide therapeutic help and multiple medical benefits for a number of other diseases besides pressure injuries. This novel, integral, holistic approach that includes physically and psychological treatment is effective. Although powered managed therapeutic surface support system 100 is designed primarily as a frontal attack on pressure injuries, it can also help other diseases treatments as well.

Figure 13:
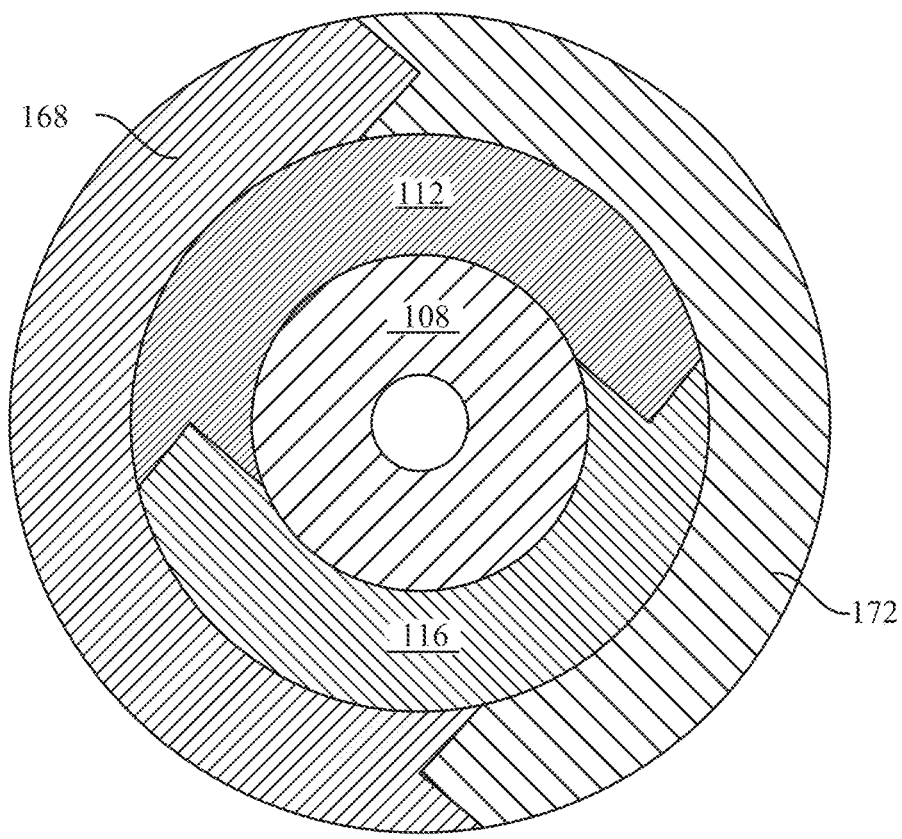
FIG. 13 is a physical representation of the combined physical and psychoneuroimmunological approach of the system.

Now referring to FIG. 13, the circle chart shows the importance in the design of the simultaneous use of a physical approach 168 and psychoneuroimmunological approach 172 used for the support system. Not only does the figure show the integration of both physical approach 168 and psychoneuroimmunological approach 172, but the components of the system used to achieve these approaches is illustrated: integrated system 104 comprising mechatronic array 108, hardware 112, and software 116. Physical approach 168 comprises the mechatronic array 108, which includes the physical components directly helping the treatment of injuries, such as the chambers, conduits, etc. as explained in FIGS. 1-6. Physical approach 168 is carried out through the managing of the physical characteristics of the main chambers that make up part of the therapeutic support surface, complying optimally with the guidelines of the world authorities specialized in pressure injuries. On the other hand, psychoneuroimmunological approach 172 comprises of hardware 112 and software 116 to achieve deep mental relaxation, which optimizes the treatment of injuries through the improvement of brain function as explained through FIGS. 2, 11, and 12. Brain function includes a link between the brain system, endocrine system, and immune system. Combining all of these components results in an innovative, frontal attack on pressure injuries through both a physical therapeutic approach 168 and psychoneuroimmunological therapeutic approach 172.

This surface could also be helpful in treating depression, distress, and anxiety through a psychoneuroimmunological approach. Psychoneuroimmunological therapeutic benefits further interact along with the said managed physical characteristics of the main chambers. Psychoneuroimmunology is the study of the relation between the brain, nervous system, and the immune system. Powered managed therapeutic surface support system 100 strengthens immune system, lessens anxiety and stress, improves mood and behavior through its ability to relax the mental state of the user and trigger neuroendocrine activity. Powered managed therapeutic surface support system 100 is configured to create a profound state of mental relaxation, which may trigger, in a non-limiting example, the strengthening of the immune system, diminishing stress, and improve mood and behavior of the user. The previously explained managed physical characteristics provides natural, ample, soft, and perfected contact of the body contour with a reduced and uniform pressure distribution. This pressure distribution can be useful for the elderly, users with reduced mobility, geriatrics, psychiatry, palliative care, long-term care, dementia, and those in burn or post operatory conditions. In addition to all this, the soothing warmth and massage can be beneficial for arthritis, rheumatism, back pain, and joint and muscle pain, among others. The surface—in addition of pressure injuries—is a therapeutic tool with clear and immediate clinical impact, thus contributing to the medical armamentarium.

The foregoing has been a detailed description of illustrative embodiments of the invention. Various modifications and additions can be made without departing from the spirit and scope of this invention. Features of each of the various embodiments described above may be combined with features of other described embodiments as appropriate to provide a multiplicity of feature combinations in associated new embodiments. Furthermore, while the foregoing describes several separate embodiments, what has been described herein is merely illustrative of the application of the principles of the present invention. Additionally, although methods herein may be illustrated and/or described as being performed in a specific order, the ordering is highly variable within ordinary skill to achieve systems and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A powered managed therapeutic support surface system for a treatment of pressure injuries, comprising:
   an integrated system for a concurrent physical and psychoneuroimmunological therapeutic approach over a user, wherein the integrated system comprises:
      an independent fluid-filled main chamber, made of waterproof, flexible, extendable, and elastic material, wherein the independent fluid-filled chamber includes an inductance sensor placed at a bottom and outside of the independent fluid-filled main chamber; and
      at least two accessory chambers fluidically connected to the main chamber through a first free-flow conduit and a second free-flow conduit;
   a powered mechatronic array configured to manage the integrated system, said powered mechatronic array being controlled by hardware and software based on microcontrollers; and
   multidisciplinary devices including a motorized positioning system, wherein said mechatronic array is configured for simultaneous operation of the multidisciplinary devices.

2. The powered managed therapeutic support surface system of claim 1, wherein the physical therapeutic approach of the concurrent physical and psychoneuroimmunological therapeutic approach over the user occurs as a function of a plurality of managed physical characteristics of the independent fluid-filled main chamber.

3. The powered managed therapeutic support surface system of claim 1, wherein the independent fluid-filled main chamber is transversely positioned relative to the user and configured to receive a weight of the user, wherein the independent fluid-filled main chamber encloses a variable amount and type of fluid, wherein the variable amount and type of fluid is adjusted as a function of a weight of a body area of the user.

4. The powered managed therapeutic support surface system of claim 1, wherein the at least two accessory chambers includes a first accessory chamber with transfer power control configured to receive or return a filling fluid from the connected main chamber.

5. The powered managed therapeutic support surface system of claim 4, wherein the independent fluid-filled main chamber is configured to adjust to a change in volume variation in the first accessory chamber or a displacement of a relative vertical position of the first accessory chamber.

6. The powered managed therapeutic support surface system of claim 1, wherein the inductance sensor is configured to limit a maximum immersion of the user and variations of a first accessory chamber of the at least two accessory chambers.

7. The powered managed therapeutic support surface system of claim 1, wherein the second free-flow conduit comprises an upper end and a lower end.

8. The powered managed therapeutic support surface system of claim 7, wherein the second free-flow conduit is non-collapsible and is positioned vertically, wherein the lower end of the second free-flow conduit is connected to the independent fluid-filled main chamber, and wherein the second free-flow conduit is fluid-filled to maintain a preset initial hydraulic head.

9. The powered managed therapeutic support surface system of claim 7, wherein the at least two accessory chambers includes a second accessory chamber fluidically connected to the upper end of the second free-flow conduit.

10. The powered managed therapeutic support surface system of claim 9, wherein the second accessory chamber is configured to be empty to dissipate a pulse or a counter-pressure from the independent fluid-filled main chamber.

11. The powered managed therapeutic support surface system of claim 1, wherein the concurrent psychoneuroimmunology therapeutic approach of the concurrent physical and psychoneuroimmunological therapeutic approach over the user comprises simultaneously operating the multidisciplinary devices to induce the user into a relaxed mental state.

12. The powered managed therapeutic support surface system of claim 11, wherein the multidisciplinary devices include a fluid temperature control system with temperature sensors and at least one fluid heater.

13. The powered managed therapeutic support surface system of claim 12, wherein the at least one fluid heater is positioned underneath the independent fluid-filled main chamber, and wherein the at least one fluid heater is fully grounded.

14. The powered managed therapeutic support surface system of claim 12, wherein the at least one fluid heater includes an insulated liquid-proof heating coil with thermostat settings controlled by the user.

15. The powered managed therapeutic support surface system of claim 11, wherein the multidisciplinary devices include a massage system.

16. The powered managed therapeutic support surface system of claim 15, wherein the massage system comprises multiple points of pulsating fluid using vibrating eccentric micromotors controlled by the user through a selection of programs, intensity, frequency, time, and active zones.

17. The powered managed therapeutic support surface system of claim 11, wherein the multidisciplinary devices include a sound system device.

18. The powered managed therapeutic support surface system of claim 17, wherein the sound system device comprises smart stereo speakers paired with the integrated system for streaming connection configured to play preprogrammed lists of sounds to engage an attention of the user and transport a mind of the user to a state of relaxation.

19. The powered managed therapeutic support surface system of claim 1, wherein the hardware and software based on microcontrollers comprises a mobile touch screen coupled to the integrated system and configured to permit the user to monitor and adjust one or more of the multidisciplinary devices of the integrated system.

20. The powered managed therapeutic support surface system of claim 19, further comprising an Internet of Things (IoT) connection in a mobile touch screen of the microcontrollers.

21. The powered managed therapeutic support surface system of claim 1, wherein the powered mechatronic array is assembled in a solid structure.

22. The powered managed therapeutic support surface system of claim 21, wherein the powered mechatronic array comprises multidisciplinary electric and electronic elements, at least one sensor, and at least one synchronized linear actuator.

23. The powered managed therapeutic support surface system of claim 1, further comprising a software program stored in an embedded microcontroller of the microcontrollers of the integrated system, wherein the embedded microcontroller is configured to control a temperature across various zones, perform different massages, play audio, and position the user to be induced into a relaxed mental state.

24. The powered managed therapeutic support surface system of claim 23, further configured to control a surface pressure, an immersion, and an envelopment of the user, for the concurrent physical and psychoneuroimmunological therapeutic approach.

* * * * *